United States Patent [19]

Bertini Curri

[11] Patent Number: 5,280,020

[45] Date of Patent: Jan. 18, 1994

[54] DRUG AND METHOD FOR INCREASING THE MICROCIRCULATORY FLOW-RATE AND VOLUME IN THE CAPILLARIES TO THE SKIN

[76] Inventor: Sergio Bertini Curri, Via Cagliero, 17-20125 Milan, Italy

[21] Appl. No.: 369,145

[22] Filed: Jun. 21, 1989

[30] Foreign Application Priority Data

Nov. 16, 1988 [IT] Italy .................... 22640 A/88

[51] Int. Cl.⁵ ............... A61K 31/685; A61K 31/40; A61K 31/66
[52] U.S. Cl. ......................... 514/78; 514/103; 514/121; 514/119; 514/114; 514/428; 548/413
[58] Field of Search ........... 514/428, 844, 929, 103, 514/78, 121, 119, 114; 548/413

[56] References Cited

U.S. PATENT DOCUMENTS

| 3,895,030 | 7/1975 | Lafon | 514/929 |
| 4,742,051 | 5/1988 | Muirhead et al. | 514/114 |

FOREIGN PATENT DOCUMENTS

| 0167825 | 1/1986 | European Pat. Off. | 514/78 |
| 0204987 | 12/1986 | European Pat. Off. | 514/78 |
| 2122144 | 5/1971 | Fed. Rep. of Germany | . |
| 2134218 | 8/1972 | France | 514/428 |
| 2539626 | 7/1984 | France | . |

OTHER PUBLICATIONS

The Merck Index, 10th ed. (Merck & Co., Inc.) (Rahway, N.J.) pp. 779-780 (1983).
A. Colantuoni et al., Changes in Arteriolar Vasomotion of Syrian hamster Skeletal Muscle Microcirculation, Italy, 1989.
A. Colantuoni et al., Quantitation of Rhythmic Diameter Changes in Arterial Microcirculation, 1984, American Physiological Society.
"Phospholipids, Chemistry, Metapolism and Function" by Answell et al., Elsevier Publishing Company, 1951, pp. 26-28.

*Primary Examiner*—Mukund J. Shah
*Assistant Examiner*—E. C. Ward
*Attorney, Agent, or Firm*—Birch, Stewart, Kolasch & Birch

[57] ABSTRACT

A drug is described which includes a physico-chemical complex between molecules of a phospholipid and an aminoketone derivative of fluoroglucinol which is useful, particularly when administered topically in the form of a liposomal aqueous microdispersion, for increasing the microcirculatory flow-rate and volume in the capillaries to the skin, both in normal conditions and in peripheral vasculopathy (primary or secondary Raynaud's disease), acrocyanosis and blocked arteries caused by arteriosclerosis, diabetes or endoangioitis obliterans.

3 Claims, 3 Drawing Sheets

DRUG AND METHOD FOR INCREASING THE MICROCIRCULATORY FLOW-RATE AND VOLUME IN THE CAPILLARIES TO THE SKIN

DESCRIPTION

The present invention relates to a drug which is useful for increasing the microcirculatory flow-rate and volume in the capillaries to the skin and, more particularly, to a drug of the above type which achieves the increase in the microcirculatory flow-rate and volume by means of increased arterio-arteriolar vaso-motion.

Amongst the drugs which are classified as peripheral vasodilators and which are more widely used in the treatment of functional and organic peripheral vasculopathy, aminoketone derivatives of fluoroglucinol 4-(pyrrolidinyl)-1(2,4,6-trimethoxyphenyl)-1-butanone; 2′,4′,6′-trimethoxy-4-(1′-pyrrolidinyl) butyrophenone; (2,4,6-trimethoxyphenyl) (3-pyrrolidinopropyl)ketone are those which are also widely used for improving microcirculation.

Drugs of this type having the general formula $C_{17}H_{26}ClNO_4$ (in the hydrochloride form) are fully described in German Pat. 2,122,144 (1971), in U.S. Pat. No. 3,895,030 (1971) and in Italian patent No. 1,120,968 and those to which the present invention particularly relates are marketed as buflomedil hydrochloride and sold under the trade names BUFENE (I.C.I.), LOFTIL (ABBOT), BUFLAN (PIERREL), IRRODAN (BIOMEDICA FOSCANA) and FLOMED (PULITZER).

According to the most current interpretation, the mechanism by which drugs of the aforesaid type act is thought to be based on a calcium-antagonistic effect whereby they interfere with the transmembrane transfer of calcium in the smooth arterial muscles or act on platelet sludging and on erythrocyte deformability: this results in activity on peripheral arterial circulation and, secondly, in an increase in local blood flow with a consequent re-establishment of the microcirculatory function.

In contrast to this interpretation, which involves a considerable technical prejudgement, it has been postulated that the actual effect of the drug is attributable to a primary and pre-eminent vasculokinetic action on the smooth muscles of the smallest precapillary arteries and arterioles of the preterminal microcirculation. This action would enable the volume and flow-rate in the tributary capillary networks to increase by increasing arterio-arteriolar vaso-motion without significantly affecting the larger arterial branches or the haemorheological factors of the microcirculation, which would have a wholly secondary or accessory role.

If this interpretation were confirmed, one would be dealing with a microvasculokinetic effect proper in which the *pumping action* (sphygmic activity) of the small preterminal arterioles and arteries is enhanced and the vascularisation of the tributary capillary networks is improved, with a consequent improvement in tissue metabolism.

Surprisingly, it has been possible to ascertain, by very sophisticated instrumental techniques (Laser-Doppler Flowmetry, infra-red Photo-Pulse Plethysmography, High-Performance Contact Thermography), that the administration of the drug to an organic site such as the skin, where only the small arteries and arterioles of the cutaneous subpapillary plexus respond to a pharmacological stimulus and it is these responses that can be evaluated by the above techniques, is followed by a statistically-significant increase in precapillary vasomotion both in physiological conditions and in functional and organic peripheral vasculopathy.

According to the present invention, a drug is provided which can increase the microcirculatory flow-rate and volume in the capillaries to the skin, characterised in that it is constituted by a complex formed between molecules of a phospholipid selected from the group consisting of lecithin, cephalin, phosphatidylserine, mono- and di-phosphoinositide, and phosphatidic acid and an aminoketone derivative of fluroglucinol known by the name of buflomedil hydrochloride and having the formula:

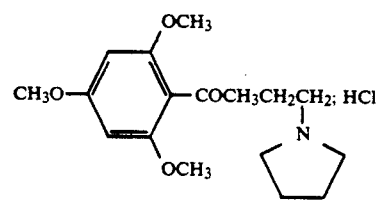

To advantage, the drug of the invention is preferably included in a liposomal aqueous microdispersion.

The drug of the invention must be administered in accordance with so-called *transdermal* criteria, that is, by its topical application, with suitable structural modifications which enable it to pass easily through the epidermal barrier, reach the dermis and achieve its microvasculokinetic effect from this position.

It is, in fact known that the pharmacokinetic activity of a substance introduced into the dermis is very different from that obtainable by oral, parenteral or intravenous administration.

In general, cessation is slow, the effects last considerably longer and, above all, fewer side effects are seen for a given administered dose.

On a clinico-therapeutic plane, this method of administration has undoubted advantages for the following reasons:

a) the methods of application are easy and repeatable
b) administration can be prolonged over a period of time, account being taken of the chronic and progressive nature of the vasculopathic processes in question.

According to a preferred embodiment, the *transdermal* administration of the drug by the epicutaneous route occurs after the physico-chemical complexing bonds have formed between the phospholipid vector molecules and the aminoketone derivative of the fluoroglucinol selected.

Previous studies by the author have shown that these complexing bonds occur between some phospholipids and, for example, organic compounds having a cyclopentane-perhydrophenanthrenic nucleus, polyphenols and anthocyanins, some oligomers and dimers of glucosaminoglycanes, some triterpenes and triterpene esters, gangliosides and some polyunsaturated fatty acids with vasokinetic activity.

In the specific case, in order to show the formation of a complex between buflomedil hydrochloride, which has the formula (1) given above, and a purified phospholipid such as, for example, lecithin, electrophoretic techniques were set up with the use of gels containing chromatographic SDS polyacrylamide prepared by the Author. The electrophoretic behaviour of the buflomedil hydrochloride PC complex was compared with that of various other phospholipid liposome preparations. The complex gave a single characteristic band at approximatley 215 kD, remote from and differerent from the characteristic patterns of non-complexed liposomes. Even after extraction with petroleum ether and acid methanolysis, the band corresponding to the complex was different when compared with the (3H) distribution in the non-bonded fatty-acid fraction, and with a standard preparation of palmitic acid methyl ester. The buflomedil hydrochloride PC bond was found to be covalent since it was unstable both when treated with 1M hydroxylamine for 24 hours and with 0.2M KOH in methanol for 30 minutes.

The invention also relates to the method or use of the drug constituted by a complex which can be formed between phospholipid molecules and an aminoketone derivative of fluoroglucinol.

EXAMPLE of the preparation of a drug according to the invention.

Purified lecithin, cephalin or phosphatidylserine were reacted with an aminoketone derivative of fluoroglucinol in a molar ratio of 0.5 to 2.

Firstly liposomal microdispersions of the said phospholipids were prepared and, after the pH had been adjusted to 4.8-5.2 and the microdispersion produced by sonication, appropriate quantities of the aminoketone derivative were added at a temperature below 45° C. After filtration through suitable "millipore" filters, the product was lyophilised by conventional techniques to give a yellowish-white powder which was only slightly soluble in water and more readily soluble in organic solvents.

Complex phospholipid: aminoketone derivatives of fluoroglucinol were thus obtained and were partially hydrophilic in character due to the fact that the polar part of the phospholipid molecule is not concerned in the bond.

The formation of the complex was confirmed by NMR spectroscopy which showed consistent variations in the $C^{13}$ spectrum of the carbon atoms in the complexed molecule as well as in those of the choline or glycerine residue whilst, in the $P^{31}$ spectrum, changes were observed in the P band compared with non-complexed phospholipids.

A liposomal aqueous microdispersion containing 30 mg/ml of the complex in distilled water was prepared from each of the complexes obtained.

This microdispersion appeared as an opalescent liquid with a pale lemon-yellow colour and was stable with time after the addition of preservatives and antimicrobial agents such as imidazolinidyl urea, isothiazolinone chloride or others.

It was observed that the epicutaneous application of the aqueous microdispersion of the drug of this invention thus obtained, in which the phospholipid-aminoketone derivative of fluoroglucinol had assumed a liposomal form, penetrated the epidermis rapidly, simply with slight massaging, leaving the surface dry, smooth, soft, resilient and velvety; after a few minutes, a sensation of subparesthesia (slight formication) and a sensation of heat were noticed, without any sign of reddening of the skin.

BEHAVIOUR of the blufomedil hydrochloride PC complex in a cellular context or in organs.

One of the more recent techniques for measuring the integrity of liposomes in cells or even directly in organs (for example the skin), without the need to remove them from the system, is that of calculation of variations in the angular spectroscopic correlation of two gamma rays emitted in the transformation of $In^{111}$ into $Cd^{111}$.

The high turnover of $In^{111}$ in the chelated form within the liposomes in fact decreases if the liposomes break; the $In^{111}$ thus released bonds rapidly with other macromolecules enabling the liposome fraction which has remained intact to be measured easily. After the intravenous injection of the complex into Sprague-Dawley male rats, the release of $In^{111}$ into the serum at 37° C. was monitored by the PAC technique. Blood samples (1 ml) were taken by cardiac puncture and the percentage of the liposomes remaining intact and bonded to blufomedil hydrochloride was calculated by the angular variation factor G22 (HI), this being compared with the same percentage of liposomes without the drug. It was assumed that the value of the liposomes in a buffer was 0.59 and that of $In^{111}$ in bovine foetal serum was 0.1, these values being assumed to correspond to 100% and 0% intact liposomes respectively. This technique requires the liposomes to contain a large quantity of $In^{111}$, not less than 10 micro Ci per micromole of liposomal lipids.

The equivalent of 10 micro Ci (1 Ci=37 GBq) of $In^{111}$ per micromole was first dried and then rehydrated with 30 ml of 3 mM HCl and 0.5 ml of a solution of 15 mM of acetylacetone in tris buffer at pH 7.6 (10 micromoles TRIS-hydroxymethylaminomethane/145 mM NaCl).

2 ml of liposomal microdispersion under test were added to this solution and were incubated at 37° C. for 60 minutes. The presence of acetylacetone, which is an ionophore, enables $In^{111}$ to cross the phosopholipd membrane of the liposome and then to be chelated within the liposome by the nitrosotriacetic acid. With this procedure, more than 80% of the $In^{111}$ was effectively intrapolated; $In^{111}$ which had not bonded was removed by passage through a column.

Preliminary studies have shown that the half life of the serum is very short and that it is eliminated very rapidly with the urine.

Since, in the experience of the Author, the recovery of radioactive In from the serum was 80% of the initial dose administered, it may be concluded that $In^{111}$ remained in the liposomes and that the percentage of liposomal vesicles bonded to buflomedil hydrochloride and remaining intact in the circulating blood is very high, equal to 90%.

The Author's study shows that the buflomedil hydrochloride complexed with PC tends, surprisingly, to be released from the bond following a fairly slow turnover which results in an actual delaying effect.

INSTRUMENTAL DEMONSTRATION of the effects.

Figure 1:
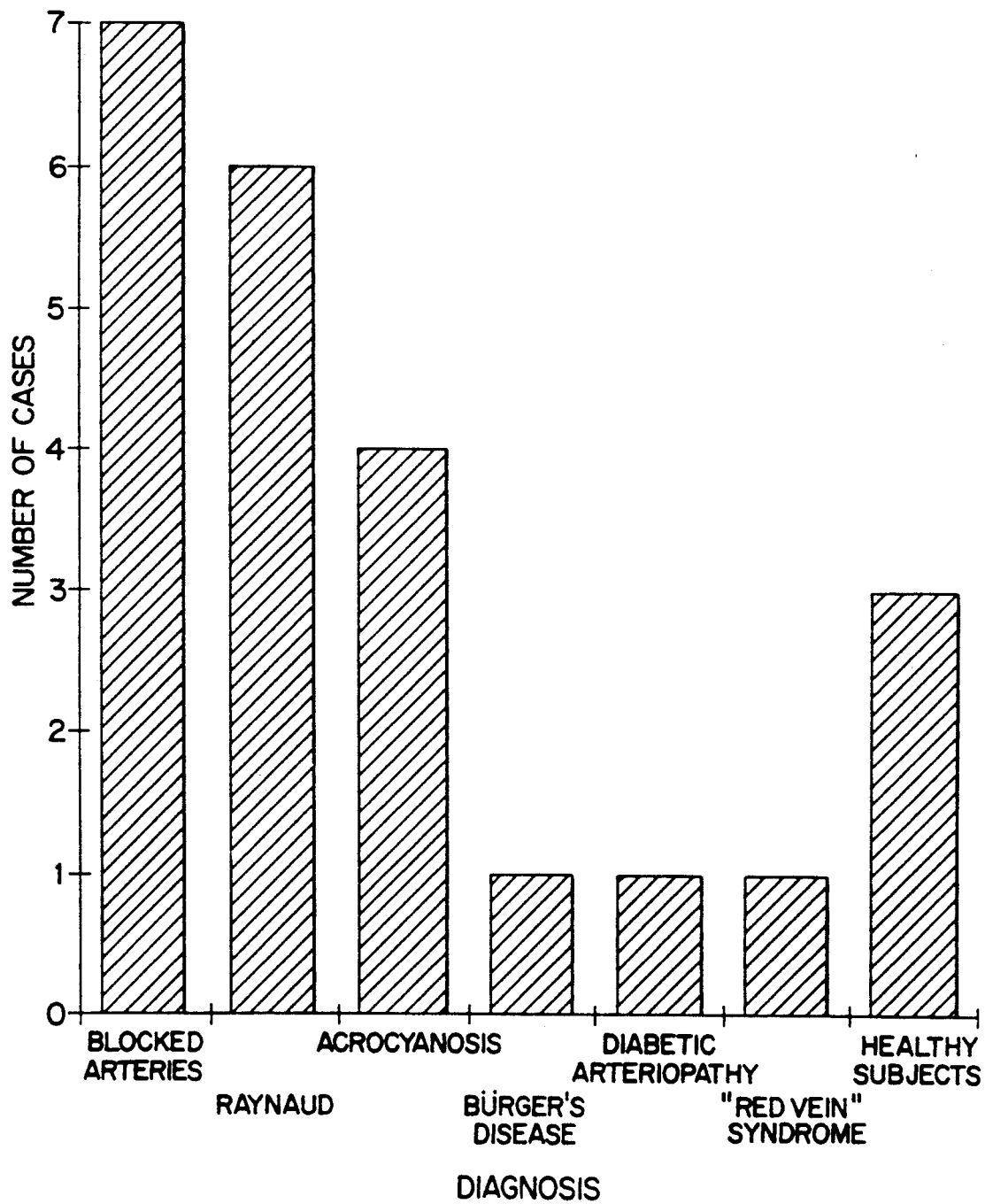
FIG. 1 is an illustration of the condition of 23 test persons.

The experiment was carried out on 23 voluntary subjects with ages varying from 32 to 67 years, of whom three were presumed healthy. The rest suffered from blocked arteries in the lower limbs, diabetic arteriopathy, thromboangitis obliterans, primary or secondary Raynoud's disease, acrocyanosis, "red vein" syndrome (see FIG. 1).

A single dose (1-5 ml) of the microdispersion of the drug of the invention was applied topically to these subjects on the skin of the hands, the cheeks, the arm and the forearm, the hand, the thigh, the legs and the feet, according to the surface of the skin area to be treated.

The instrumental evaluation of the microvasculokinetic effect and of the increase in the volume of flow in the tributary capillary networks was carried out by the following techniques;

A—direct skin thermometry
B—high-resolution contact thermography (HRCT)
C—infra-red photoplethysmography by computerised LAUMANN GMBH apparatus, (i.r. Ph.-P.P.)
D—modified laser Doppler flowmetry for evaluating the sphygmic arterio-arteriolar activity (L.D.F.)

Results

The instrumental observations were made under base conditions and 30' and 60' after application.

Mean SD values for the amplitude of the plethysmographic wave or of the Laser-Doppler trace, the mean maximum height of the LD traces, the mean minimum heights of the traces and the HFRV (high-frequency rhythmic variation) were calculated.

The results obtained for the organic peripheral vasculur acrosyndromes are summarised in Table 1.

TABLE 1

ORGANIC PERIPHERAL VASCULAR ACROSYNDROME
(areteriosclerosis obliterans, diabetic angiopathy and Buerger's disease)

|  | Laser Db | Laser I | Laser II | Meanhigh I | Meanhigh II | Meanhigh III |
|---|---|---|---|---|---|---|
| CASE Nr. 1 | 33 | 108 | 255 | 45 | 107 | 107 |
| CASE Nr. 2 | 113 | 202 | 242 | 47 | 85 | 107 |
| CASE Nr. 3 | 30 | 47 | 276 | 100 | 100 | 140 |
| CASE Nr. 4 | 71 | 151 | 131 | 70 | 72 | 80 |
| CASE Nr. 5 | 51 | 68 | 209 | 50 | 50 | 60 |
| CASE Nr. 7 | 139 | 184 | 198 | 68 | 40 | 10 |
| CASE Nr. 11 | 49 | 92 | 92 | 50 | 50 | 80 |
| CASE Nr. 12 | 9 | 19 | 291 | 80 | 45 | 100 |
| CASE Nr. 13 | 76 | 81 | 80 | 60 | 80 | 110 |
| CASE Nr. 15 | 130 | 176 | 196 | 50 | 50 | 50 |
| CASE Nr. 16 | 25 | 46 | 112 | 125 | 158 | 150 |
| CASE Nr. 17 | 24 | 84 | 87 | 79 | 80 | 80 |
| MEAN | 62.5 | 104.8333333 | 180.75 | 68.66666667 | 76.41666667 | 89.5 |
| DEV. STD. | 42.03669032 | 57.45408795 | 74.0710526 | 23.34999405 | 32.49732895 | 36.9402671 |

|  | Meanlow I | Meanlow II | Meanlow III | HFR VI | HFR VII | HFR VIII |
|---|---|---|---|---|---|---|
| CASE Nr. 1 | 37 | 70 | 60 | 35 | 60 | 60 |
| CASE Nr. 2 | 17 | 45 | 65 | 30 | 40 | 100 |
| CASE Nr. 3 | 92 | 80 | 110 | 30 | 100 | 180 |
| CASE Nr. 4 | 30 | 50 | 50 | 30 | 30 | 30 |
| CASE Nr. 5 | 30 | 30 | 20 | 90 | 90 | 150 |
| CASE Nr. 7 | 50 | 40 | 70 | 50 | 50 | 80 |
| CASE Nr. 11 | 40 | 40 | 40 | 30 | 40 | 60 |
| CASE Nr. 12 | 70 | 40 | 50 | 40 | 40 | 90 |
| CASE Nr. 13 | 40 | 40 | 50 | 20 | 50 | 90 |
| CASE Nr. 15 | 30 | 30 | 20 | 80 | 30 | 160 |
| CASE Nr. 16 | 100 | 135 | 130 | 60 | 60 | 60 |
| CASE Nr. 17 | 67 | 65 | 60 | 70 | 110 | 90 |
| MEAN | 50.25 | 55.41666667 | 60.41666667 | 47.08333333 | 58.33333333 | 95.83333333 |
| DEV. STD. | 25.18307964 | 28.31801056 | 30.85303425 | 21.8382628 | 26.08745974 | 43.48531042 |

TABLE 2

FUNCTIONAL PERIPHERAL VASCULAR ACROSYNDROME
(Raynaud's disease, acrocyanosis)

|  | Laser Db | Laser I | Laser II | Meanhigh I | Meanhigh II | Meanhigh III |
|---|---|---|---|---|---|---|
| CASE Nr. 6 | 80 | 87 | 165 | 60 | 50 | 70 |
| CASE Nr. 8 | 81 | 109 | 230 | 60 | 90 | 150 |
| CASE Nr. 9 | 1 | 550 | 999 | 40 | 90 | 90 |
| CASE Nr. 10 | 1 | 155 | 250 | 70 | 110 | 150 |
| CASE Nr. 14 | 232 | 192 | 449 | 80 | 50 | 100 |
| MEAN | 79 | 218.6 | 418.6 | 62 | 78 | 112 |
| DEV. STD. | 84.3587577 | 169.6521146 | 305.3185877 | 13.26649916 | 24 | 32.49615362 |

|  | Meanlow I | Meanlow II | Meanlow III | HFR VI | HFR VII | HFR VIII |
|---|---|---|---|---|---|---|
| CASE Nr. 6 | 40 | 30 | 40 | 50 | 60 | 90 |
| CASE Nr. 8 | 50 | 60 | 40 | 100 | 130 | 150 |
| CASE Nr. 9 | 30 | 40 | 40 | 50 | 130 | 110 |
| CASE Nr. 10 | 60 | 80 | 90 | 50 | 120 | 150 |
| CASE Nr. 14 | 40 | 30 | 30 | 70 | 40 | 90 |
| MEAN | 44 | 48 | 48 | 64 | 96 | 118 |
| DEV. STD. | 10.19803903 | 19.39071943 | 21.3541565 | 19.59591794 | 38.26225294 | 27.12931993 |

From these it emerged that, from base mean values of 62.5+42.03, values of 104.83+57.45 were detected at the first reading and 180.75+74.07 at the third reading.

Figure 2:
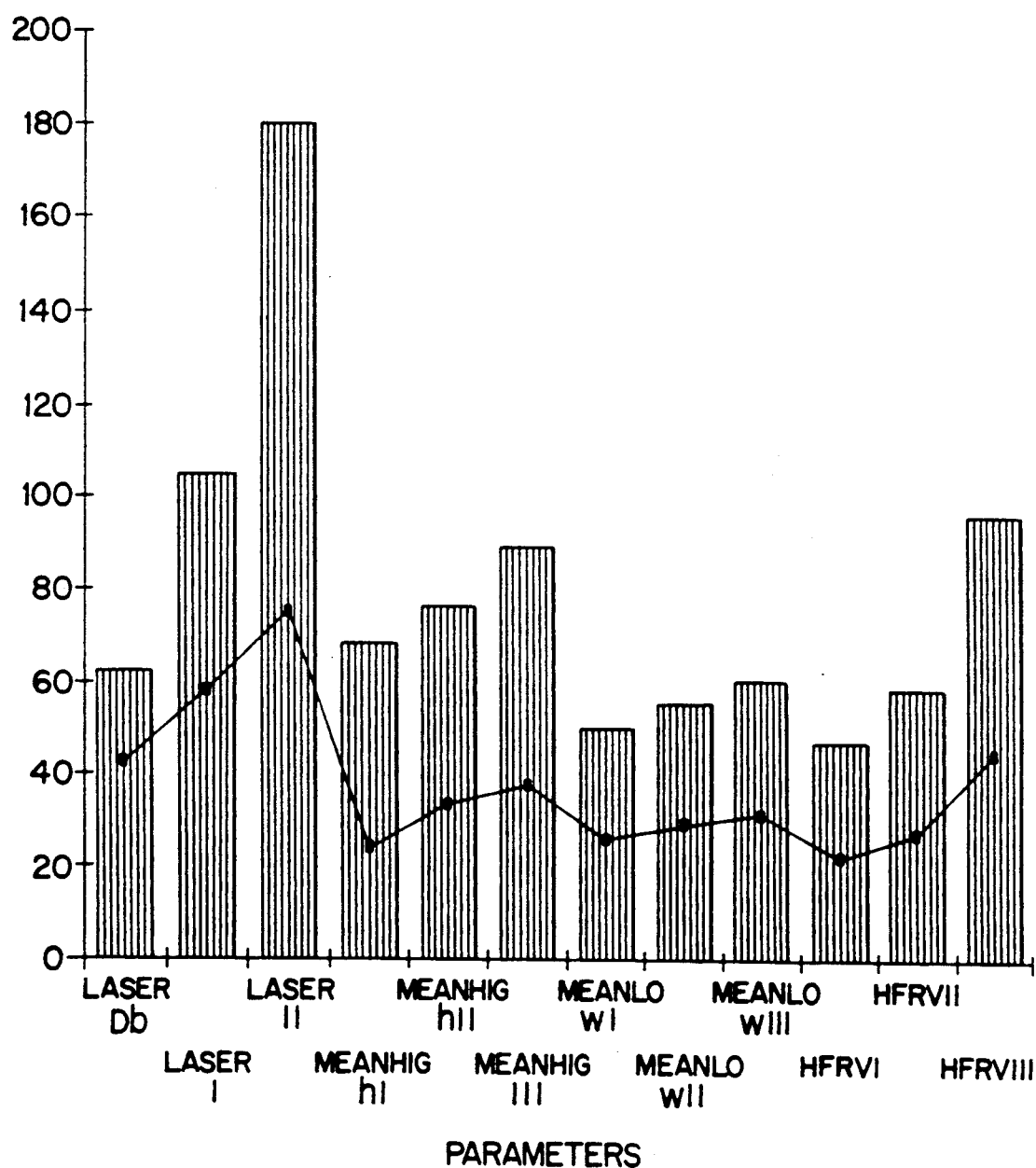
FIG. 2 is an illustration of the organic peripheral vascular acrosyndromes corresponding to the figures as tabulated in Table 1.

As is seen from FIG. 2, 60' from the beginning of the treatment, the values of the area subtended, and hence the arterio-arteriolar vaso-motion covered, had increased to more than about 300% of the base values.

The mean maximum ranges of the peaks had also increased from 68.66+23.84 to 89.5+36.9.

The mean value of the minimum heights of the peaks had also increased in a similar manner, although to a less marked extent, from 50.25+25.18 to 60.41+30.85 and that of the HFRV had increased from 47.08+21.83 to 95.83+43.48 (see FIG. 2).

Figure 3:
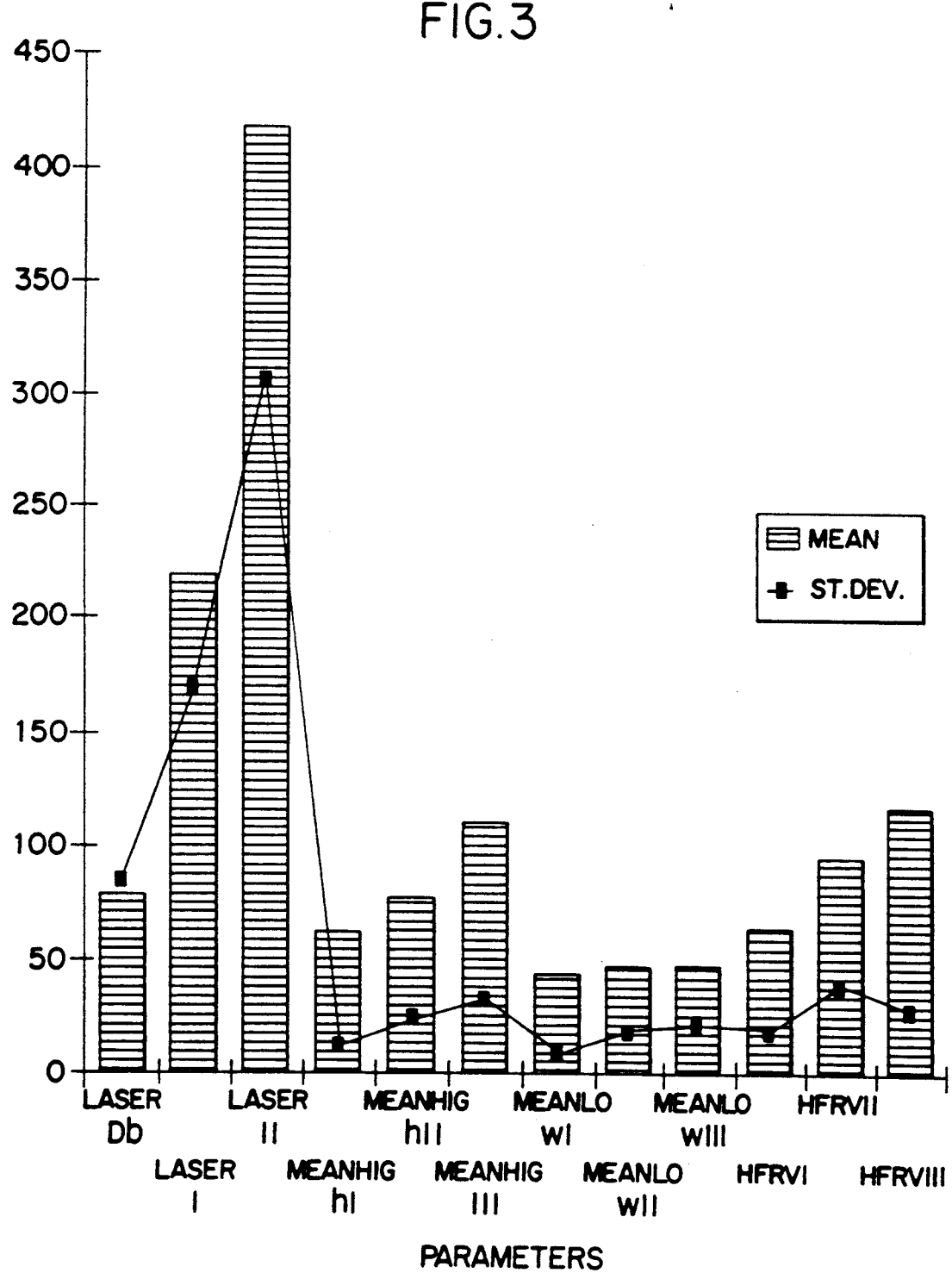
FIG. 3 is an illustration of the functional peripheral vascular acrosyndromes corresponding to the figures as tabulated in Table 2.

In the functional peripheral vascular acrosyndromes, the improvement in the amplitude of the Sphygmic ranges was much more impressive, with mean values which changed from 79.0+84.35 to 418.6+305.35 (see Table 2 and FIG. 3).

All the other parameters were modified similarly (see FIG. 3.).

The laser-Doppler instrumental variations show that the epicutaneous application of the complex induced a statistically significant increase in the microcirculatory flow volume, with better perfusion of the capillary networks, implying an improvement in microvascular-tissue correlation and hence in tissue trophism and metabolism.

The results of direct skin thermometry and high-resolution contact thermography show an increase in skin temperature which varies from 0.5° to 2° C. and can be correlated with an opening of the capillary networks before relaxation, and hence with an increase in the microcirculatory flow-rate and volume without any reddening (phenomena of active congestion) or side effects.

The infra-red photoplethysmography (i.r. Ph.P.P.) carried out with the LAUMANN GmbH apparatus confirms the laser Doppler results, it having been possible to detect statistically-significant increases in the amplitudes of the sphygmic waves, together with modifications in their shape, which indicate an increase in the microcirculatory flow.

Over all, these variations in the parameters of the arterio-arteriolar vaso-motion were documented both in healthy subjects, regardless of the part of the skin subjected to the experiment, and in subjects suffering from organic or functional peripheral vasculopathy. Moreover, the arterio-arteriolar vaso-motion of a further seven subjects affected by alopecia areata was determined under base conditions by infra-red photoplethysmography and skin thermography as well as contact thermography.

After epicutaneous application of the complex constituting the drug of the invention, at a concentration of 1% (in an aqueous microdispersion) a statistically-significant increase in the amplitude and shape of the trace was detected, as well as an increase in skin temperature which lasted longer than 60'.

This implies an increase in the vascularisation of the hair roots.

In parallel, it was noted that the liposomal microdispersion of the drug of the invention has a substantive effect on the hair and an anti-seborrhoeic effect which enables the frequency of washing to be reduced in subjects with alopecia seborrhoeica. This effect is thought to be due to the phospholipid component of the complex.

A further 108 cases of functional or organic peripheral vascular acrosyndrome were also tested.

In primary or secondary Raynoud's disease, a considerable reduction was observed in the number and duration of acroasphyctic crises and of syncopal pain after treatment for 30 days with 2-3 vials per day of the preparation of buflomedil hydrochlorfide PC applied epicutaneously and made to penetrate the skin surface of the hand and the forearm by slight massaging.

In femoro-popliteal or subpopliteal blocked arteries with cyanosis, oedema and pain, epicutaneous treatment for 33 days with 3 vials per day resulted in resolution of the oedema, a marked decrease in cyanosis and a net reduction in the pain.

In blocked arteries resulting from arteriosclerosis, diabetes or blocked arteries from endoangioitis obliterans, with intermittent limping and a cold feeling in the legs and the knees, the treatment induces considerable clinical improvements, particularly as regards walking pace and pain reduction.

Instrumental checks before and after treatment were carried out by LASER-DOPPLER flowmetry (PERIMED-PF2B-Stockholm) and by infra-red plethysmography.

The digital plethysmographic curves of the areas under test (the fleshy parts of the fingers and/or of the toes) showed quite surprising results. In several cases of Raynoud's disease, in addition to the nett subjective improvement with the disappearance of pain, the morphological normalisation of the plethysmographic curves was also recorded. In many cases of peripheral blocked arteries, after suitable periods of treatment, the LASER-DOPPLER flowmetry shows an often considerable improvement in the local microcirculatory flow-rate and volume parameters. The data collected under pathological conditions confirm the assumptions of the tests carried out on the first group of healthy subjects and on the second group of subjects suffering from peripheral vascular acrosyndrome.

The present invention is also directed to a cosmetic product, particularly for the treatment of unsightly skin resulting from deficient capillary vascularization, characterized in that it is constituted by a complex formed between molecules of a phospholipid selected from the group comprising (lecithin, cephalin, phosphatidylserine, phosphoinositide and phosphatidic acid) and an aminoketone derivative of fluoroglucinol, known as buflomedil hydrochloride and having the general formula:

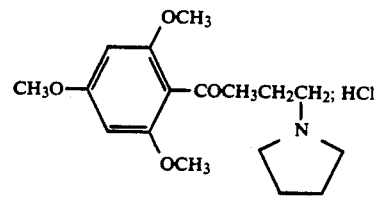

The present invention is also directed to a cosmetic product characterized in that it is in the form of a cream, an ointment, a pomade, a gel, an emulsion or the like.

I claim:

1. A method for the topical treatment of alopecial conditions of the hairy skin, of the cheeks and of the chin which comprises applying an effective amount of buflomedil hydrochloride having the formula:

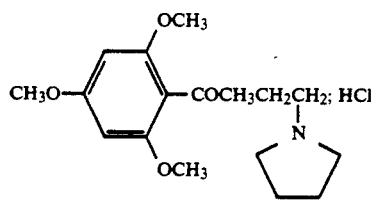

wherein said buflomedil hydrochloride is in the form of a physico-chemical complex with a phospholipid selected from the group consisting of lecithin, cephalin, phosphatidylserine, phosphoinositide, and phosphatidic acid, or mixtures thereof in the form of a cream, an ointment, a pomade, a gel, or an emulsion to the area to be treated.

2. A method for increasing the microcirculatory flow-rate and volume in the capillaries to the skin, which comprises administering a transepidermal effective amount of buflomedil hydrochloride having the formula:

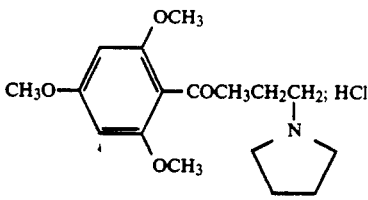

wherein said buflomedil hydrochloride is in the form of a physico-chemical complex with a phospholipid selected from the group consisting of lecithin, cephalin, phosphatidylserine, phosphoinositide, and phosphatidic acid, or mixtures thereof.

3. The method according to claim 2, wherein said physico-chemical complex formed between said buflomedil hydrochloride and at least one phospholipid is in the form of a liposomal aqueous dispersion.

* * * * *